United States Patent [19]

Axelsson

[11] 4,364,730

[45] Dec. 21, 1982

[54] PERIDONTAL PROBE

[76] Inventor: Per A. T. Axelsson, Drottninggatan 27, S-652 25 Karlstad, Sweden

[21] Appl. No.: 313,490

[22] Filed: Oct. 21, 1981

[30] Foreign Application Priority Data

Oct. 31, 1980 [SE] Sweden ................................ 8007684

[51] Int. Cl.³ ................................................. A61C 3/00
[52] U.S. Cl. ..................................... 433/141; 433/72; 433/147
[58] Field of Search .................... 433/72, 75, 141, 146, 433/147; 128/776

[56] References Cited

U.S. PATENT DOCUMENTS

| 560,702 | 5/1896 | Flaherty | 433/147 |
| 656,300 | 8/1900 | Perry | 433/141 |
| 904,990 | 11/1908 | Powers | 433/147 |
| 1,229,024 | 6/1917 | Brandt | 433/147 |
| 1,406,143 | 2/1922 | Bates | 433/147 |
| 3,935,640 | 2/1976 | Cohan | 433/75 |
| 4,203,223 | 5/1980 | Lautenschlager et al. | 433/141 |

FOREIGN PATENT DOCUMENTS

| 508703 | 10/1930 | Fed. Rep. of Germany | 433/147 |
| 818228 | 7/1949 | Fed. Rep. of Germany | 433/72 |
| 564471 | 12/1923 | France | 433/147 |
| 7703431 | 10/1978 | Netherlands | 433/72 |
| 615339 | 1/1980 | Switzerland | 433/146 |

Primary Examiner—Paul J. Hirsch
Assistant Examiner—John J. Wilson
Attorney, Agent, or Firm—Cushman, Darby & Cushman

[57] ABSTRACT

A peridontal probe comprising a handle portion and a pin member rotatably mounted thereon about an axis of rotation, the pin member having a free end portion which is straight and flat, lies wholly to one side of and in the same plane as the axis of rotation, the spacing between the free end portion and the axis either being constant or decreasing in a direction towards the free end of the free end portion.

8 Claims, 7 Drawing Figures

U.S. Patent  Dec. 21, 1982  4,364,730
FIG.1
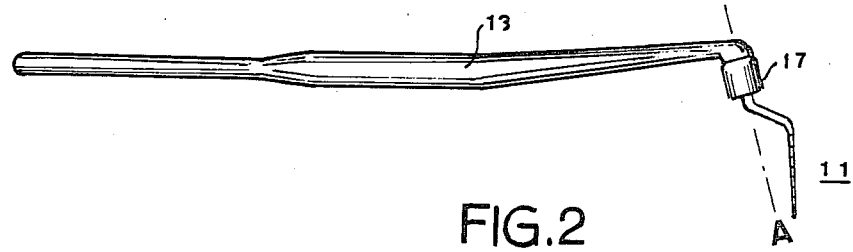
FIG.4
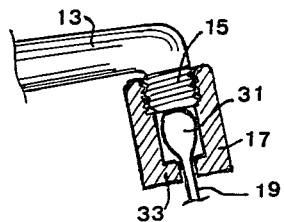
FIG.2
FIG.3
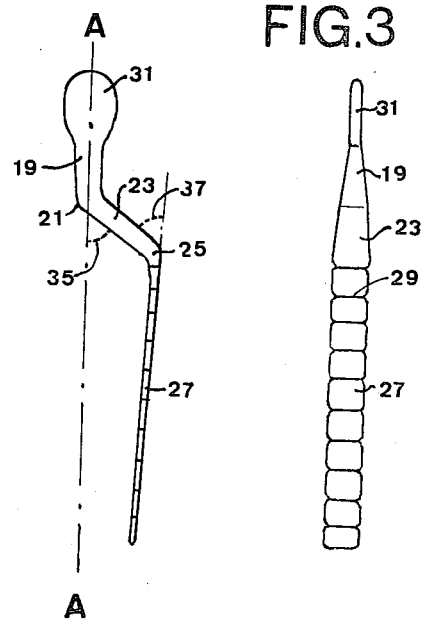
FIG.5
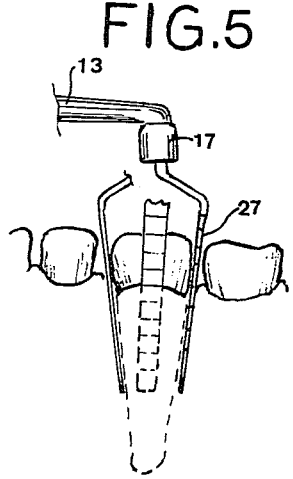
FIG.6     FIG.7
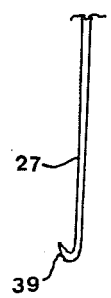
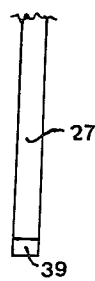

PERIDONTAL PROBE

BACKGROUND OF THE INVENTION

The present invention relates to a peridontal probe, that is to say, a dental instrument used for examining whether or not tartar and/or calculus are present in the peridontal cavity or whether there has been any loss of the peridontal attachment tissue.

Known instruments of this type generally comprise a pin-like member which is suitably shaped for insertion into the peridontal cavity of a patient, the pin member being mounted on one end of a handle portion so that the probe can be manipulated.

In most known instruments, the pin member is fixedly attached to, and forms an extension of, the handle portion. However, the pin member is bent intermediate its ends so that the free end portion thereof remote from the handle extends at an angle of substantially 45° to the longitudinal axis of the handle. When used for investigating the peridontal cavities of a patient, the end portion of the pin member is pushed downwardly into the peridontal cavity, between a tooth and the gum, until an increased resistance is felt. This occurs when the pin member strikes against the bottom of the cavity. The depth of the pocket can be readily ascertained if the pin member is provided with graduated markings. A dentist is usually particularly interested in ascertaining how far the cavity extends beyond the boundary between the tooth enamel and the root cementum, from which can be ascertained how much of the peridontal tooth-to-bone attachment fibers in the peridontal space has been lost. Furthermore, such an instrument is suitable for detecting whether tartar has been deposited on the root faces of the tooth in the peridontal cavity.

Ordinarily, the effective portion of the pin member which is used for determining such measurements is of circular cross-section. However, the width of the peridontal cavity is often of the order of a few tenths of a millimeter. Accordingly, it is generally advisable to use an instrument having a flattened end portion so as not to damage the tissue when inserting the probe and also to ensure that the bottom of the peridontal cavity is reached by the pin member. However, probes of such design can only be used for investigating the tongue and cheek faces of the teeth. It is therefore necessary to use another type of instrument having a circular cross-section pin member when probing the interdental regions of the cavities. This is particularly true when probing the rear teeth of a patient because the angle at the corner of the mouth prevents the dentist from holding the handle portion at the correct angle.

The present invention seeks to provide an instrument having a flat portion suitable for determining the above-described measurements but which is suitable for probing the cavities on all sides of the teeth.

BRIEF SUMMARY OF THE INVENTION

In principle, this aim is achieved by attaching the pin member in a rotatable manner to the handle, so that the flat face portion thereof used for measuring can be brought into contact with any side of the tooth and can automatically be adjusted so that it is located at the correct angle for insertion into the narrow slit between the tooth and the gum without causing trauma to the patient.

According to the present invention, there is provided a peridontal probe for the investigation of a peridontal cavity comprising a handle portion and a pin member, the pin member being rotatably mounted on the handle portion so as to be rotatable about an axis of rotation, the pin member having a straight, flat, free end portion suitable for insertion into a peridontal cavity, the free end portion lying wholly to one side of the axis of rotation and being co-planar therewith, the spacing between the free end portion and the axis of rotation being constant or reducing in a direction towards the free end of the free end portion.

BRIEF DESCRIPTION OF THE DRAWINGS

Two embodiments of the present invention will be further described, purely by way of example, with reference to the accompanying drawings, in which:

FIG. 1 is a lateral view of a probe in accordance with the present invention;

FIGS. 2 and 3 show, respectively, a side elevation and a plan view, of the pin member forming part of the probe shown in FIG. 1 but on an enlarged scale relative thereto;

FIG. 4 shows a cross-sectional view through a portion of the probe shown in FIG. 1 but on an enlarged scale relative thereto and showing the attachment of the pin member to a handle portion;

FIG. 5 shows, schematically, the manner in which the probe is used, and

FIGS. 6 and 7 show, respectively, an elevational view and a plan view of a modified embodiment of the end portion of the pin member.

DESCRIPTION OF THE PREFERRED EMBODIMENTS

As shown in FIG. 1, a probe in accordance with the present invention comprises a pin member 11 and a handle portion 13, by means of which the probe is held and manipulated. The handle portion 13 has a bent-over end portion 15 which is screw-threaded and is engaged in a threaded socket 17 in which the pin member 11 is held. The mounting of the member 11 in the socket 17 is such that the member 11 can be rotated through 360° about the axis A—A. The axis A—A subtends an angle of 90° or more but preferably less than 120° to the handle portion 13.

The pin member 11 comprises an elongate, thin, stiff steel member, the configuration thereof being shown more clearly in FIGS. 2 and 3. The member 11 has two bends 21 and 25 therein such that, overall, it is generally of a Z-shape. However, the three portions 19, 23 and 27 all lie in one and the same plane. The straight portion 19 is used for attaching the pin member 11 to the handle portion 13 and extends to the first bend 21. Between the two bends 21 and 25 is a straight portion 23 extending obliquely to the portion 19. From the second bend 25, which is oppositely directed to the bend 21, to the free end of the member 11 is a further straight portion 27. The portion 27 is preferably graduated in millimeters by a series of transverse impressions 29, thus forming a measuring rule. The end portion 27 is flattened over the majority, if not all, of its length. It is of a substantially rectangular cross-section. Ideally, it has a width of 0.2 to 0.3 mm and a thickness of 1.5 mm. The length of the end portion 27 is preferably about 15 to 18 mm, although the length over which it is graduated may be somewhat less. The attachment portion 19 and the intermediate portion 23 are each either round in cross-section or have a cross-section which is less flat than the portion 27. The portions 19 and 23 may be as thick as or even thicker than the measuring or free end portion 27. The end of the portion 19 which is connected to the handle portion is flattened to form an oval disc 31. When the instrument is assembled, the disc 31 extends diametrically across the cylindrical bore of the socket 17, whilst at least a portion of the main body of the portion 19 projects and is fitted into a central aperture formed in the base 33 of the socket 17. The socket maintains the disc 31 applied against an end portion 17 of the handle 13 or adjacent thereto. In this manner, the pin member is held so as to be free to rotate through 360° without restriction whilst still being guided so that its rotation occurs around the axis A—A.

The measuring or free end portion 27 is located in the same plane as the axis A—A, but is located laterally thereof. It may extend parallel to such axis but as shown, it is preferred if it extends obliquely relative thereto with the free end lying closer the axis. The connecting portion 23 extends at an angle 35 of between 30° and 60° relative to the attachment portion 19, which extends along the axis A—A. The angle 37 between the connecting portion 23 and the measuring portion 27 is about equal not more than 15° greater than the angle 35. The connecting part 23 is shorter than the measuring portion 27 but is sufficiently long that the tip of measuring portion is located at a distance from the axis A—A which is somewhat less than half the width of a tooth crown, that is to say, between 2 and 4 mm. The broad side faces of the measuring portion 27 extend at right angles to the plane of the probe pin, that is to say, the plane of the paper if the probe is viewed as shown in FIG. 2. The disc 31 is shown located in the plane, but may be inclined thereto, if desired.

FIG. 5 shows the probe being used for measuring the depth of the peridontal cavity on different faces of a tooth. The position shown in full lines shows the measurement being effected at the interdental space on one side of the tooth, and the partially drawn positions shows the measurement at the opposite interdental side and at the tongue or cheek side of the tooth, respectively. Due to its flattened design and the above-mentioned size of the measuring portion, the probe can be readily inserted even when the tooth is closely surrounded by the gum. The cross-sectional dimension of the probe is sufficiently great for the dentist to be able to percieve clearly when the probe has hit the bottom of the peridontal cavity.

If a pin member with a circular cross-section is used, and a narrow cavity is probed, there is the risk that the gum will be damaged or that the dentist encounters a resistance before the probe reaches the bottom of the cavity. On the other hand, if a probe pin having a smaller circular cross-section is used, there is the risk that the penetrating of the probe is too simple and the probe may be inserted too far into the weak tissue at the bottom of the peridontal cavity, thereby giving a spurious result of the measured depth of the cavity.

When the dentist applies the measuring portion of the probe against the side of the crown of a tooth and then moves the probe into a position so that the socket 17 is located approximately opposite the centre of the crown, the pin member automatically rotates about the axis A—A until the broad face of the measuring portion 27 lies closely adjacent the side of the tooth. The pin member can then be displaced in the longitudinal direction of the tooth and the measuring portion thereof can be inserted into the slit-like peridontal pocket whilst being guided therein. Using an instrument having a flattened pin portion extending at a fixed angle to the handle portion, there is the risk that the probe will be inserted so that its cross-section extends at an angle to the narrow peridontal space, thereby harming the gum tissue.

After partial or full retraction of the measuring portion of the probe, it can be moved by the dentist into other positions around the same tooth by slightly pivoting and longitudinally displacing the handle portion. Whilst the probe is still inserted into the mouth of the patient in substantially the same location, the pin member is automatically adjusted in accordance with the orientation of the tooth face so when the probe is being displaced into a new measurement position, the broad face of the free end portion of the pin member can be maintained in continuous contact with the tooth and move in an arcuate path therearound.

If the instrument is to be used for investigating the presence of tartar on a tooth root in the peridontal cavity, the free end portion of the pin member is provided with a small, sharply ground, hook 39, as is shown in FIGS. 6 and 7. A separate pin member is preferably used for this purpose. This need not be graduated and which is connected to the handle portion in the same way as, but in place of, the pin member shown in FIGS. 2 and 3.

The majority of measurements of the probe given above are not critical, but are merely examples of suitable values which obviously may be varied to suit individual requirement, the attachment of the probe pin may also be modified without departing from the scope of the invention as set forth in the appendant claims.

I claim:

1. A peridontal probe for the investigation of a peridontal cavity comprising a handle portion, a pin member rotatably mounted on said handle portion about an axis of rotation, said pin member having a first and second end portion, said first end portion carrying attachment means for rotatably mounting said pin member on said handle portion and said second end portion being a free end portion and being straight and flat and terminating in a free end, said free end portion lying wholly to one side of said axis of rotation and being co-planar therewith, to define a space therebetween, said spacing between said free end portion and said axis of rotation being constant.

2. A peridontal probe for the investigation of a peridontal cavity comprising a handle portion, a pin member rotatably mounted on said handle portion about an axis of rotation, said pin member having a first and second end portion, said first end portion carrying attachment means for rotatably mounting said pin member on said handle portion and said second end portion being a free end portion and being straight and flat and terminating in a free end, said free end portion lying wholly to one side of said axis of rotation and being co-planar therewith, to define a space therebetween, said spacing between said free end portion and said axis of rotation reducing in a direction towards said free end of said free end portion.

3. A probe as recited in claim 1 or 2, wherein said free end portion is of rectangular cross-section.

4. A probe as recited in claim 1 or 2 wherein said handle portion has a longitudinal axis, said axis of rotation subtending an angle of between 90° and 120° with said longitudinal axis of said handle portion.

5. A probe as recited in claim 1 or 2 wherein said free end portion of said pin member carries a series of graduated markings.

6. A probe as recited in claim 1 or 2 wherein said pin comprises first, second and third portions, said first portion being straight and having first and second ends, said first end of said first portion carrying attachment means rotatably mountable on said handle portion, a first bend portion provided on said second end of said first portion, said second portion being straight and having first and second ends, said first end of said second portion terminating at said first bend portion, a second bend portion provided on said second end of said second portion and said third portion having first and second ends, said first end terminating at said second bend portion, said second end of said third portion being a free end.

7. A probe as recited in claim 6, wherein said first end of said first portion is flattened to form a disc, said disc being located in the plane of said pin member, socket means fixedly connected to said handle portion, said socket means being hollow and including a base portion, said base portion defining a central recess, said disc being located in and guided by, said socket means, said first portion of said pin member projecting through said central recess, said disc and said socket jointly forming said rotatable mounting for said pin member on said handle member.

8. A probe as recited in claim 6 wherein the supplement of the angle subtended between said first portion and said second portion at said first bend porton and the supplement of the angle between said second portion and said third portion at said second bend portion are both between 30° and 60°, the difference between said two supplementary angles being a maximum of 15°.

* * * * *